(12) United States Patent
Han

(10) Patent No.: US 9,221,813 B2
(45) Date of Patent: Dec. 29, 2015

(54) INTERMEDIATES AND PROCESSES FOR PREPARING COMPOUNDS

(71) Applicant: Genentech, Inc., South San Francisco, CA (US)

(72) Inventor: Chong Han, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/396,346

(22) PCT Filed: Apr. 22, 2013

(86) PCT No.: PCT/US2013/037646
§ 371 (c)(1),
(2) Date: Oct. 22, 2014

(87) PCT Pub. No.: WO2013/163109
PCT Pub. Date: Oct. 31, 2013

(65) Prior Publication Data
US 2015/0105557 A1    Apr. 16, 2015

Related U.S. Application Data

(60) Provisional application No. 61/637,170, filed on Apr. 23, 2012.

(51) Int. Cl.
*C07D 401/10* (2006.01)
*C07D 471/04* (2006.01)

(52) U.S. Cl.
CPC ..................... *C07D 471/04* (2013.01)

(58) Field of Classification Search
CPC ..................................... C07D 401/10
USPC ........................................ 546/113
See application file for complete search history.

(56) References Cited

U.S. PATENT DOCUMENTS

2015/0011533 A1*   1/2015   Stokes et al. ............ 514/210.21

FOREIGN PATENT DOCUMENTS

| WO | WO 2007/072017 A2 | 6/2007 |
| WO | WO 2008/144253 A1 | 11/2008 |
| WO | 2009089352 | * 7/2009 |
| WO | WO 2009/089352 A1 | 7/2009 |
| WO | WO 2009/089359 A1 | 7/2009 |
| WO | 2009140320 | * 11/2009 |
| WO | WO 2009/140320 A1 | 11/2009 |

OTHER PUBLICATIONS

Ahn et al., "The Chk2 protein kinase", *DNA Repair* 3, 1039-1047 (2004).
Bartek et al. "CHK2 Kinase—A Busy Messenger", *Nature Reviews Molecular Cell Biology*, vol. 2 (12), 877-886 (2001).
Janetka et al., "Inhibitors of checkpoint kinases: From discovery to the clinic", *Drug Discovery & Development* vol. 10 (4), 473-486 (2007).
Patent Cooperation Treaty, International Searching Authority, Search Report and Written Opinion for PCT/US203/037646, 10 pages, Jul. 3, 2013.
Pommier et al., "Targeting Chk2 Kinase: Molecular Interaction Maps and Therapeutic Rationale", *Current Pharmaceutical Design*, vol. 11 (22), 2855-2872 (2005).
Tse et al., "Targeting Checkpoint Kinase 1 in Cancer Therapeutics", *Clin. Cancer Res.* 13 (7), 1955-1960 (2007).

* cited by examiner

*Primary Examiner* — Niloofar Rahmani
(74) *Attorney, Agent, or Firm* — Viksnins Harris & Padys PLLP

(57) ABSTRACT

The invention provides intermediates and processes of preparation thereof useful in the preparation of compounds that can be used as CHK1 inhibitors.

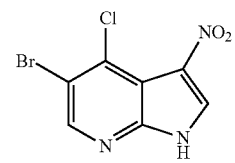

15 Claims, No Drawings

INTERMEDIATES AND PROCESSES FOR PREPARING COMPOUNDS

RELATED APPLICATIONS

This application claims the benefit of priority of provisional U.S. Application No. 61/637,170 filed 23 Apr. 2012, which is hereby incorporated by reference in its entirety.

FIELD OF THE INVENTION

In an aspect, the present invention relates to intermediate compounds and processes for making these intermediate compounds. The intermediates compounds are useful for making compounds with anti-cancer activity, for example compounds which inhibit CHK1 kinase activity.

BACKGROUND OF THE INVENTION

Protein kinases are kinase enzymes that phosphorylate other proteins. The phosphorylation of these proteins usually produces a functional change in the protein. Most kinases act on serine and threonine or tyrosine, and some kinases act on all three. Through these functional changes, kinases can regulate many cellular pathways. Protein kinase inhibitors are compounds that inhibit these protein kinases, and thus can be used to affect cellular pathways.

Checkpoint kinase 1 ("CHK1") is a serine/threonine kinase. CHK1 regulates cell-cycle progression and is a main factor in DNA-damage response within a cell. CHK1 inhibitors have been shown to sensitize tumor cells to a variety of genotoxic agents, such as chemotherapy and radiation. (Tse, Archie N., et al., "Targeting Checkpoint Kinase 1 in Cancer Therapeutics." Clin. Cancer Res. 13(7) (2007) 1955-1960). It has been observed that many tumors are deficient in the G1 DNA damage checkpoint pathway, resulting in the reliance on S and G2 checkpoints to repair DNA damage and survive. (Janetka, James W., et al., "Inhibitors of checkpoint kinases: From discovery to the clinic." Drug Discovery & Development Vol. 10, No. 4 (2007) 473-486).

The S and G2 checkpoints are regulated by CHK1. Inhibition of CHK1 has been shown to cancel the S and G checkpoints, thereby impairing DNA repair and resulting in increased tumor cell death. However, non-cancerous cells have a functioning G checkpoint, allowing for DNA repair and survival.

Checkpoint kinase 2 ("CHK2") is also a serine/threonine kinase. CHK2's functions are central to the induction of cell cycle arrest and apoptosis by DNA damage. (Ahn, Jinwoo, et al., "The Chk2 protein kinase." DNA Repair 3 (2004) 1039-1047). CHK2 is activated in response to genotoxic insults and propagates the checkpoint signal along several pathways, which eventually causes cell-cycle arrest in the G1, S and G2/M phases, activation of DNA repair, and apoptotic cell death. (Bartek, Jiri, et al., "CHK2 Kinase—A Busy Messenger." Nature Reviews Molecular Cell Biology. Vol. 2(12) (2001) 877-886). Cancer cells often lack one or more genome-integrity checkpoints, so inhibition of CHK2 could make tumor cells selectively more sensitive to anti-cancer therapies, such as γ-radiation or DNA-damaging drugs.

Normal cells would still activate other checkpoints and recover, while cancer cells deprived of checkpoints would be more likely to die. It has been demonstrated that a peptide-based inhibitor of CHK2 abrogated the G2 checkpoint and sensitized p53-defective cancer cells to DNA damaging agents. (Pommier, Yves, et al., "Targeting Chk2 Kinase: Molecular Interaction Maps and Therapeutic Rationale." Current Pharmaceutical Design. Vol. 11, No. 22 (2005) 2855-2872).

CHK1 and/or CHK2 inhibitors are known, see for example, International Publication WO 2009/089352, WO2009/089359 and WO2009/140320.

SUMMARY OF THE INVENTION

An aspect of the invention relates to 5-bromo-4-chloro-3-nitro-1H-pyrrolo[2,3-b]pyridine of Formula I:

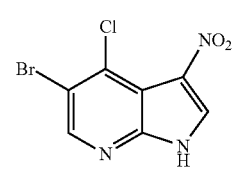

and stereoisomers, tautomers and pharmaceutically acceptable salts thereof 5-bromo-4-chloro-3-nitro-1H-pyrrolo[2,3-b]pyridine of Formula I can be useful as an intermediate compound in a process for preparing compounds which can be used as Chk1 inhibitors.

Another aspect of the invention relates to processes for preparing 5-bromo-4-chloro-3-nitro-1H-pyrrolo[2,3-b]pyridine of Formula I.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. The invention is intended to cover all alternatives, modifications, and equivalents which may be included within the scope of the present invention. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

Definitions

The words "comprise" "comprising" "include" "including" and "includes" when used in this specification and in the following claims are intended to specify the presence of stated features, integers, components, or steps, but they do not preclude the presence or addition of one or more other features, integers, components, steps, or groups thereof.

The term "alkyl" includes linear or branched-chain radicals of carbon atoms.

Some alkyl moieties can be referred to in an abbreviated form, for example, methyl ("Me"), ethyl ("Et"), propyl ("Pr") and butyl ("Bu"), and further abbreviations are used to designate specific isomers of compounds, for example, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu") and the like. In a certain embodiment, alkyl groups can be $C_1$-$C_6$-alkyl groups. i.e. alkyl groups having 1 to 6 carbon atoms. In a certain embodiment, alkyl groups can be $C_1$-$C_4$-alkyl groups. In a certain embodiment, alkyl groups can be $C_1$-$C_3$-alkyl groups. The abbreviations are sometimes used in conjunction with elemental abbreviations and chemical structures, for example, methanol ("MeOH") or ethanol ("EtOH").

The term "cycloalkyl" as used herein refers to As used herein, the term "cycloalkyl" refers to a saturated or partially saturated, monocyclic, fused polycyclic, bridged polycyclic, or spiro polycyclic carbocycle having from 3 to 15 ring carbon atoms. A non limiting category of cycloalkyl groups are saturated or partially saturated, monocyclic carbocycles having from 3 to 6 carbon atoms. Illustrative examples of cycloalkyl groups include, but are not limited to, the following moieties:

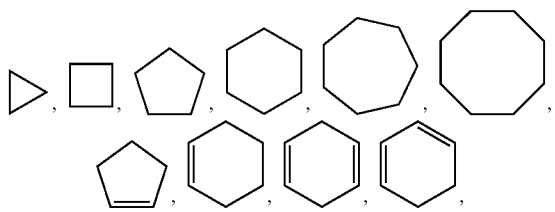

Additional abbreviations that may be used throughout the application include, for example, benzyl ("Bn"), phenyl ("Ph") and acetate ("Ac").

The terms "heterocycle" and "heterocyclic" include four to seven membered rings containing one, two or three heteroatoms selected from the group consisting of oxygen, nitrogen and sulfur. In certain instances, these terms may be specifically further limited, such as, "five to six membered heterocyclic" only including five and six membered rings. Exemplary heterocyclic groups include, but are not limited to, oxiranyl, thiaranyl, aziridinyl, oxetanyl, thiatanyl, azetidinyl, 1,2-dithietanyl, 1,3-dithietanyl, tetrahydrofuranyl, tetrahydrothiophenyl, dithiolanyl, pyrrolidinyl, pyrazolidinyl, imidazolidinyl, 1,3-dioxolanyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, thioxanyl, oxepanyl, thiepanyl, azepanyl, 1,4-dioxepanyl, 1,4-oxathiepanyl, 1,4-oxaazepanyl, 1,4-dithiepanyl, 1,4-thieazepanyl, and 1,4-diazepanyl.

Exemplary partially unsaturated heterocyclic groups include, but are not limited to, tetrahydropyridinyl, dihydropyridinyl, dihydropyranyl, dihydrofuranyl, 1-pyrrolinyl, 2-pyrrolinyl, 3-pyrrolinyl, 2H-pyranyl, 4H-pyranyl, and pyrazolinyl.

The term "heteroaryl" includes five to six membered aromatic rings containing one, two or three heteroatoms selected from the group consisting of oxygen, nitrogen and sulfur.

In certain instances, these terms may be specifically further limited, such as, five to six membered heteroaryl, wherein the heteroaryl contains one or two nitrogen heteroatoms.

Exemplary heteroaryl groups include, but are not limited to, pyrrolyl, furanyl, thiophenyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, pyrazinyl, furazanyl, and triazinyl.

The terms "treat" or "treatment" refer to therapeutic, prophylactic, palliative or preventative measures. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

The expressions "therapeutically effective amount" or "effective amount" mean an amount of a compound of Formula IV that, when administered to a mammal in need of such treatment, sufficient to (i) treat or prevent the particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound that will correspond to such an amount will vary depending upon factors such as the particular compound, disease condition and its severity, the identity (e.g., weight) of the mammal in need of treatment, but can nevertheless be routinely determined by one skilled in the art.

The terms "cancer" and "cancerous" refer to or describe the physiological condition in mammals that is typically characterized by abnormal or unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer (including small-cell lung cancer, non-small cell lung cancer ("NSCLC"), adenocarcinoma of the lung and squamous carcinoma of the lung), cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, skin cancer, including melanoma, as well as head and neck cancer.

The expression "pharmaceutically acceptable" indicates that the substance or composition is compatible chemically and/or toxicologically, with the other ingredients comprising a formulation, and/or the mammal being treated therewith.

The expression "pharmaceutically acceptable salt," as used herein, refers to pharmaceutically acceptable organic or inorganic salts of a compound of the invention.

The compounds of this invention also include other salts of such compounds which are not necessarily pharmaceutically acceptable salts, and which may be useful as intermediates for preparing and/or purifying compounds of this invention and/or for separating enantiomers of compounds of this invention.

The term "mammal" means a warm-blooded animal that has or is at risk of developing a disease described herein and includes, but is not limited to, guinea pigs, dogs, cats, rats, mice, hamsters, and primates, including humans.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of Formulas I to XI described herein may contain asymmetric or chiral centers, and therefore exist in different stereoisomeric forms. It is intended that all stereoisomeric forms of the compounds of Formulas I to XI described herein, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The expression "pharmaceutically acceptable salt" as used herein, refers to pharmaceutically acceptable organic or inorganic salts of a compound of Formulas I to XI described herein. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1′-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If a compound of Formulas I to XI described herein is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If a compound of Formulas I to XI described herein is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A "solvate" refers to an association or complex of one or more solvent molecules and a compound of Formulas I to XI described herein. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

CHK1/2 Inhibitors

The intermediate according to the invention can be useful in the preparation of certain substituted pyrrolo[2,3-b]pyridines, and pharmaceutical formulations thereof, that inhibit CHK1 and/or CHK2 such as for example described in WO2009/140320. These compounds are potentially useful in the treatment of diseases, conditions and/or disorders modulated by CHK1 and/or CHK2.

Preparation of Compounds

The compounds described herein may contain asymmetric or chiral centers, and therefore exist in different stereoisomeric forms. It is intended that all stereoisomeric forms of the compounds of Formulas I to XI described herein, including but not limited to, diastereomers, enantiomers and atropisomers, as well as mixtures thereof such as racemic mixtures, form part of the present invention. In addition, the present invention embraces all geometric and positional isomers. In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds described herein may exist in unsolvated as well as solvated forms with pharmaceutically acceptable solvents such as water, ethanol, and the like, and it is intended that the invention embrace both solvated and unsolvated forms.

The compounds described herein may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present described herein also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically-labeled compounds of the present invention (e.g., those labeled with $^3$H and $^{14}$C) are useful in compound and/or substrate tissue distribution assays. Tritiated ($^3$H) and carbon-14 ($^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Examples herein below, by substituting an isotopically labeled reagent for a non-isotopically labeled reagent.

Starting materials and reagents for the preparation of compounds according to the invention are generally available from commercial sources such as Sigma-Aldrich Chemical (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database).

As mentioned above, in one aspect, the invention relates to 5-bromo-4-chloro-3-nitro-1H-pyrrolo[2,3-b]pyridine of Formula I:

and stereoisomers, tautomers and pharmaceutically acceptable salts thereof.

In another aspect, the invention, relates to a process for the preparation of 5-bromo-4-chloro-3-nitro-1H-pyrrolo[2,3-b]pyridine of Formula I.

In one embodiment of the present invention, 5-bromo-4-chloro-3-nitro-1H-pyrrolo[2,3-b]pyridine of Formula I can be prepared in a process comprising the step of subjecting 4-chloro-3-nitro-1H-pyrrolo[2,3-b]pyridine of Formula II:

to a bromination.

The bromination can be performed using brominating agents known in the art, for example a brominating agent chosen from, but not limited to, bromine, pyridinium tribromide, pyridinium dichlorobromate, 1,3-dibromo-5,5-dimethylhydantoin, tetrabromocyclohexadienone or N-Bromosuccinimide (NBS). A person skilled in the art will also find that reaction conditions, solvents, reageants and other elements described in Larock, R. C. *Comprehensive Organic Transformations,* 2nd ed., Wiley-VCH, NY, 1999, pp. 619-628 can be used for aromatic brominations such as the bromination of the compound of Formula I.

4-chloro-3-nitro-1H-pyrrolo[2,3-b]pyridine of Formula II is registered as CAS# [23709-47-9] and is commercially available from Sigma Aldrich under catalog number 699268.

The bromination can be performed under acidic conditions, for example in suspension in a solvent that can be selected from an organic acid such as those know in the art, for example acetic acid. In a certain embodiment, a solvent suitable for bromination can be chosen from, but not limited to, acetic acid, DMSO, DMF, DMA, acetonitrile, methylene chloride or chloroform.

In one embodiment of the invention, the bromination of 4-chloro-3-nitro-1H-pyrrolo[2,3-b]pyridine of Formula II can be performed with N-Bromosuccinimide (NBS) as a brominating agent.

In one embodiment of the invention, the bromination of 4-chloro-3-nitro-1H-pyrrolo[2,3-b]pyridine of Formula II can be performed with N-Bromosuccinimide (NBS) as a brominating agent in suspension in acetic acid.

In one embodiment of the invention, N-Bromosuccinimide (NBS) is used in excess, e.g. about 1.60 equivalent of 4-chloro-3-nitro-1H-pyrrolo[2,3-b]pyridine.

In one embodiment of the invention, the bromination of 4-chloro-3-nitro-1H-pyrrolo[2,3-b]pyridine of Formula II can be performed with N-Bromosuccinimide (NBS) as a brominating agent suspended in acetic acid at about 25° C. for about 18 h.

In another embodiment of the invention, a process for the preparation of 5-bromo-4-chloro-3-nitro-1H-pyrrolo[2,3-b]pyridine of Formula I comprises the steps of: (a) subjecting 4-chloro-1H-pyrrolo[2,3-b]pyridine of Formula III:

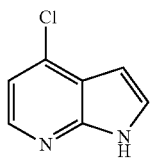

to a nitration, to yield 4-chloro-3-nitro-1H-pyrrolo[2,3-b]pyridine of Formula II:

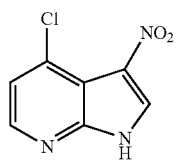

(b) and subjecting 4-chloro-3-nitro-1H-pyrrolo[2,3-b]pyridine of Formula II to a bromination to yield 5-bromo-4-chloro-3-nitro-1H-pyrrolo[2,3-b]pyridine of Formula I.

4-chloro-1H-pyrrolo[2,3-b]pyridine of Formula III is registered as CAS# [55052-28-3] and is commercially available from Sigma Aldrich under catalog number 696218.

A nitrating agent suitable for the nitration of step (b) can be nitric acid.

The nitration of step (b) can be performed in acidic conditions. In a certain embodiment, the acidic conditions are met by using sulfuric acid.

A mentioned above, 5-bromo-4-chloro-3-nitro-1H-pyrrolo[2,3-b]pyridine of Formula I can be used as a starting material or an intermediate in a process for preparing compounds of Formula IV that are useful as Chk1 inhibitors:

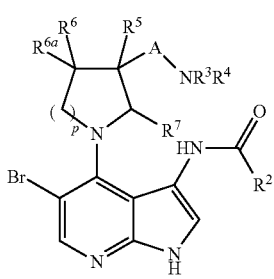

wherein:

A is selected from a direct bond or $CR^aR^b$;

$R^2$ is selected from $C_1$-$C_6$ alkyl, —O($C_1$-$C_6$ alkyl), —NH($C_1$-$C_6$ alkyl), a saturated or partially unsaturated $C_3$-$C_6$ cycloalkyl, phenyl, a saturated or partially unsaturated 4 to 6 membered heterocyclic, a 5 or 6 membered heteroaryl, an 8 to 10 membered bicyclic aryl, an 8 to 10 membered bicyclic heterocyclic, and an 8 to 10 membered bicyclic heteroaryl, wherein the alkyls, cycloalkyl, phenyl, heterocyclics, heteroaryls and aryl are optionally substituted with one or more groups selected from OH, CN, halogen, oxo (except not on phenyl, aryl or heteroaryl), $CF_3$, cyclopropyl, cyclopropylmethyl, —$SO_2R^1$, $C_1$-$C_6$ alkyl, —O($C_1$-$C_6$ alkyl), —S($C_1$-$C_6$ alkyl), $NR^eR^f$, and phenyl, wherein the phenyl is optionally substituted with one or more groups selected from OH, CN, halogen, $CF_3$, $C_1$-$C_3$ alkyl, —O($C_1$-$C_3$ alkyl), and $NR^gR^h$;

$R^3$ and $R^4$ are independently selected from hydrogen or $C_1$-$C_4$ alkyl optionally substituted with OH, F, —O($C_1$-$C_3$ alkyl) or $C_3$-$C_6$ cycloalkyl, or $R^3$ and $R^4$ together with the atoms to which they are attached form a 5 or 6 membered ring;

$R^5$ is selected from hydrogen and $CH_3$, or

A is $CR^aR^b$, $R^a$ and $R^b$ are hydrogen, and $R^3$ and $R^5$ together with the atoms to which they are attached form a 5 or 6 membered ring;

$R^6$ is selected from hydrogen, F, OH, —$OCH_3$, $C_1$-$C_3$ alkyl and cyclopropyl, or A is a direct bond, $R^{6a}$ is hydrogen and $R^3$ and $R^6$ together with the atoms to which they are attached form a 5 or 6 membered ring;

$R^{6a}$ is selected from hydrogen, F, OH, and $CH_3$;

$R^7$ is hydrogen, or

A is $CR^aR^b$ and $R^3$ and $R^7$ together with the atoms to which they are attached form a 5 or 6 membered ring;

$R^a$ is hydrogen, or $R^4$ and $R^b$ are absent and $R^3$ and $R^a$ together with the atoms to which they are attached form an aromatic 5 or 6 membered ring;

$R^b$ is hydrogen or absent;

$R^c$ and $R^d$ are independently selected hydrogen and $C_1$-$C_3$ alkyl, or $R^c$ and $R^d$ together with the atom to which they are attached form a 5 or 6 membered ring;

$R^e$ and $R^f$ are independently selected hydrogen and $C_1$-$C_3$ alkyl;

$R^g$ and $R^h$ are independently selected from hydrogen and $C_1$-$C_3$ alkyl;

$R^i$ is $C_1$-$C_3$ alkyl; and p is 0, 1, 2 or 3.

The compounds of Formula IV can be used as CHK1 inhibitors as described in WO2009/140320, the content of which is incorporated by reference herein in its entirety. In particular, 5-bromo-4-chloro-3-nitro-1H-pyrrolo[2,3-b]pyridine of Formula I can be used as a starting material or an intermediate in a process for preparing compounds the CHK1 inhibitors of WO2009/140320 which are described in examples 1, 1A, 1B, 2, 3, 3A, 4, 5, 6, 7, 15, 16, 17, 18, 19, 20 21, 22, 23, 24, 25, 26, 27, 28, 29, 30, 31, 32, 33, 34, 35, 36, 37, 38, 39, 40, 41, 42, 43, 45, 46, 47, 49, 50, 51, 52, 53, 54, 55, 56, 57, 58, 59, 60, 62, 63, 64, 65, 66, 67, 68, 69, 70, 71A, 71B, 72, 73, 75, 76, 77, 78, 83, 86, 87, 90, 90A, 90B, 93, 94, 95, 98, 99, 100, 105, 106, 108, 110, 114, 121, 123, 126, 128, 129, 130, 131, 132A, 132B, 134, 135, 136, 137, 138, 139, 140, 141, 144, 145, 146, 147, 149, 150, 151, 152, 158, 161, 162, 163, 164, 167, 168, 170, 171, 172, 173, 174, 175, 182, 183A, 183B and 184. The person skilled in the art will be able to adjust the reaction condition for the preparation of theses CHK1 inhibitors, starting from 5-bromo-4-chloro-3-nitro-1H-pyrrolo[2, 3-b]pyridine of Formula I can be used as a starting material or an intermediate in a process for preparing compounds and based on the present disclosure.

Compounds of Formula IV can be prepared, starting from 5-bromo-4-chloro-3-nitro-1H-pyrrolo[2,3-b]pyridine of Formula I, according to a process comprising the steps of:

(a) reducing a compound of Formula I:

I to yield a compound of Formula V:

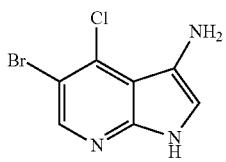

V (b) reacting the compound of Formula V with a compound of Formula VI:

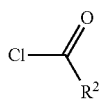

VI wherein $R^2$ is as defined above, to yield a compound of Formula VII:

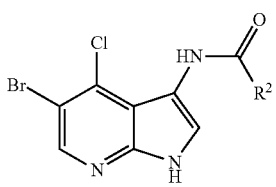

VII wherein $R^2$ is as defined above;

(c) reacting the compound of Formula VII with a compound of Formula VIII:

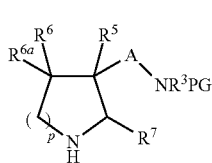

VIII wherein A, $R^3$, $R^5$, $R^6$, $R^{6a}$, $R^7$ and p are as defined above and PG is an amine protecting group;

under standard $S_NAr$ reaction conditions to yield a compound of Formula IX:

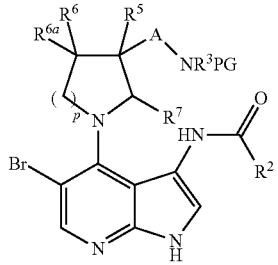

IX wherein A, $R^2$, $R^3$, $R^5$, $R^6$, $R^{6a}$, $R^7$ and p are as defined above;

(d) deprotecting the compound of Formula IX to yield the compound of Formula IV:

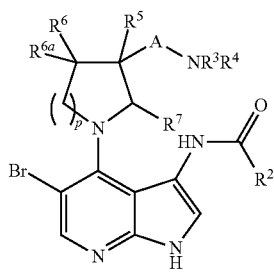

IV wherein $R^4$ is as defined above.

The conditions and reagents of schemes 2, 3, 4 and 5 of WO2009140320, the content of which is incorporated by reference, describe the preparation of compound 11 can be applied to the above process in the preparation of compounds of Formula IV.

Alternatively, compounds of Formula IV can be prepared, starting from 5-bromo-4-chloro-3-nitro-1H-pyrrolo[2,3-b]pyridine of Formula I, according to a process comprising the steps of:

(a) reacting a compound of Formula I:

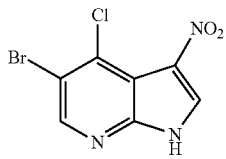

I with a compound of Formula VIII:

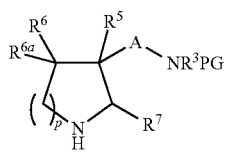

VIII wherein A, $R^3$, $R^5$, $R^6$, $R^{6a}$, $R^7$ and p are as defined above and PG is an amine protecting group;

under standard $S_NAr$ reaction conditions to yield a compound of Formula X:

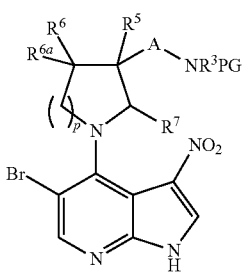

wherein A, $R^2$, $R^3$, $R^5$, $R^6$, $R^{6a}$, $R^7$ and p are as defined above;

(b) reducing the compound of Formula X to yield a compound of Formula XI:

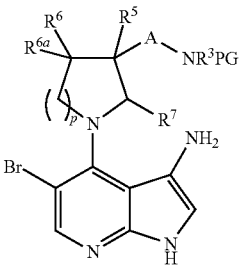

reacting the compound of Formula XI with a compound of Formula VI:

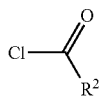

wherein $R^2$ is as defined above, to yield a compound of Formula IX:

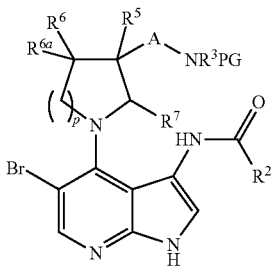

wherein $R^2$ is as defined above;

(d) deprotecting the compound of Formula IX to yield the compound of Formula IV:

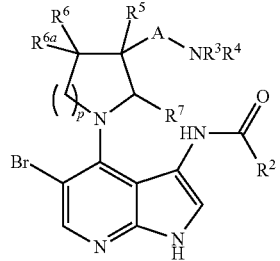

wherein $R^4$ is as defined above.

A person skilled in the art will recognize that the conditions and reagents of schemes 2, 3, 4 and 5 of WO2009140320, the content of which is incorporated by reference, can also be applied to the above process in the preparation of compounds of Formula IV.

Methods of Separation

In the methods of preparing the compounds of Formulas I to XI described herein, it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of Formulas I to XI described herein may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the of Formulas I to XI described herein can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem., (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Administration and Pharmaceutical Formulations

The compounds of Formula IV may be administered by any convenient route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal.

The compounds may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents. If parenteral administration is desired, the compositions will be sterile and in a solution or suspension form suitable for injection or infusion.

A typical formulation is prepared by mixing a compound of Formula IV and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of Formula IV or pharmaceutical composition thereof) or aid in the manufacturing of the pharmaceutical product (i.e., medicament).

One embodiment includes a pharmaceutical composition comprising a compound of Formula IV, or a stereoisomer or pharmaceutically acceptable salt thereof. A further embodiment, provides a pharmaceutical composition comprising a compound of Formula IV, or a stereoisomer or pharmaceutically acceptable salt thereof, together with a pharmaceutically acceptable carrier or excipient.

Methods of Treatment with Compounds of Formula IV

The compounds of Formula IV can be used for treating or preventing disease or condition by administering one or more compounds of Formula IV or a stereoisomer or pharmaceutically acceptable salt thereof. In one embodiment, a human patient is treated with a compound of Formula IV, or a stereoisomer or pharmaceutically acceptable salt thereof, and a pharmaceutically acceptable carrier, adjuvant, or vehicle in an amount to detectably inhibit CHK1 activity.

A method of preventing or treating a disease or disorder modulated by CHK1 and/or CHK2 can comprise administering to a mammal in need of such treatment an effective amount of a compound of Formula IV.

In another embodiment a method of treating a hyperproliferative disease in a mammal comprising administering a therapeutically effective amount of the compound of Formula IV, or a stereoisomer or pharmaceutically acceptable salt thereof, to the mammal is provided.

In another embodiment, a method of treating or preventing cancer, including the below identified conditions, in a mammal in need of such treatment, wherein the method comprises administering to said mammal a therapeutically effective amount of a compound of Formula IV, or a stereoisomer or pharmaceutically acceptable salt thereof.

In certain embodiments, the CHK1 inhibitor of Formula IV (i.e., a compound of Formula I) is administered in combination with a DNA damaging agent. Generally, the DNA damaging agent will be administered before the CHK1 inhibitor of Formula IV. DNA damaging agents include Gemzar® (gemcitabine), Camptosar® (irinotecan or CPT-11), Temodar® (temozolomide), Xeloda® (capecitabine), Hycamtin® (topotecan), cisplatin, Eloxatin® (oxaliplatin), Paraplatin®

(carboplatin), camptothecin, ara-C (cytarabine), 5-FU (fluorouracil), Cytoxan® (cyclophosphamide), Etopophos® or Vepesid® (etoposide phosphate), Vumon® (teniposide), Adriamycin PFS® or Adriamycin RDF® (doxorubicin), daunorubicin, Alimta® (pemetrexed), and radiation. In certain embodiments, the DNA damaging agent is selected from the group consisting of gemcitabine, irinotecan, temozolomide, capecitabine, camptothecin, cisplatin, ara-C, and 5-FU. In certain embodiments, the DNA damaging agent is selected from gemcitabine, irinotecan, temozolomide and capecitabine. In certain embodiments, the DNA damaging agent is selected from gemcitabine, irinotecan, cisplatin, oxaliplatin, carboplatin and cytarabine. In certain embodiments, the DNA damaging agent is selected from gemcitabine and irinotecan. The DNA damaging agent is administered at its approved or recommended dose.

Because of the ability of a CHK1 inhibitor to potentiate the activity of many anti-cancer agents it is expected that a wide range of tumor types may be treated by the compositions and methods described herein. These conditions include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; Breast: invasive breast carcinomas (invasive ductal carcinoma and invasive lobular carcinoma), etc.; and Adrenal glands: neuroblastoma. The term hyperproliferative disease includes the above identified conditions. The term "cancerous cell" as provided herein, includes a cell afflicted by any one of the above identified conditions.

In certain embodiments herein, the cancer is selected from colorectal cancer (including Ras mutations), small cell lung cancer, non-small cell lung cancer, glioma, ovarian cancer, metastatic breast cancer, pancreatic cancer, hepatobiliary cancer (including hepatocellular cancer, bile duct cancer and cholangiocarcinoma), gastric cancer, testicular cancer, head and neck squamous cell carcinoma, leukemia (including acute myeloid leukemia, acute lymphoblastic leukemia, chronic myeloid leukemia, and chronic lymphoid leukemia), lymphoma (including mantle cell lymphoma, Hodgkin's lymphoma and non-Hodgkin's lymphoma), and prostrate cancer.

In certain embodiments herein, the cancer is a solid tumor cancer.

In certain embodiments herein, the cancer is selected from pancreatic cancer, ovarian cancer and colorectal cancer.

In certain embodiments herein, the cancer is selected from colorectal cancer (including Ras mutations), small cell lung cancer, non-small cell lung cancer, and glioma. In certain embodiments, the CHK1 inhibitor is administered in combination with a DNA damaging agent. In a further embodiment, the DNA damaging agent is irinotecan.

In certain embodiments herein, the cancer is selected from non-small cell lung cancer, ovarian cancer, metastatic breast cancer, pancreatic cancer, hepatobiliary cancer (including hepatocellular cancer, bile duct cancer and cholangiocarcinoma), and gastric cancer. In certain embodiments, the CHK1 inhibitor is administered in combination with a DNA damaging agent. In a further embodiment, the DNA damaging agent is gemcitabine.

In certain embodiments herein, the cancer is selected from colorectal cancer (including Ras mutations), small cell lung cancer, non-small cell lung cancer, ovarian cancer, hepatobiliary cancer (including hepatocellular cancer, bile duct cancer and cholangiocarcinoma), gastric cancer, testicular cancer, and head and neck squamous cell carcinoma. In certain embodiments, the CHK1 inhibitor is administered in combination with a DNA damaging agent. In a further embodiment, the DNA damaging agent is selected from the group consisting of cisplatin, oxaliplatin, and carboplatin.

In certain embodiments herein, the cancer is selected from leukemia (including acute myeloid leukemia, acute lymphoblastic leukemia, chronic myeloid leukemia, and chronic lymphoid leukemia), lymphoma (including mantle cell lymphoma, Hodgkin's lymphoma and non-Hodgkin's lymphoma), and prostrate cancer. In certain embodiments, the CHK1 inhibitor is administered in combination with a DNA damaging agent. In a further embodiment, the DNA damaging agent is cytarabine.

Another embodiment herein provides the use of a compound of Formula IV, or a stereoisomer or pharmaceutically acceptable salt thereof, in the manufacture of a medicament for the treatment of cancer.

In another embodiment, a method of treating or preventing a disease or disorder modulated by CHK1 and/or CHK2, comprising administering to a mammal in need of such treatment an effective amount of a compound of Formula IV, or a stereoisomer or pharmaceutically acceptable salt thereof.

In another embodiment, a method of preventing or treating cancer, comprising administering to a mammal in need of such treatment an effective amount of a compound of Formula IV, alone or in combination with one or more additional compounds having anti-cancer properties.

CHK1 inhibitors are expected to potentiate the activity of a wide range of anti-cancer agents (or DNA damaging agents), when such agent(s) trigger the CHK1 dependent cell cycle checkpoint.

The compounds of Formula IV can be used in a composition for the treatment of a hyperproliferative disease in a mammal, wherein said composition comprises a therapeutically effective amount of a compound of Formula IV, or a stereoisomer or a pharmaceutically acceptable salt thereof, in combination with an anti-tumor agent selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, anti-androgens, targeted antibodies, HMG-CoA reductase inhibitors, and prenyl-protein transferase inhibitors.

The compounds of Formula IV can also be used in a method for the treatment of a hyperproliferative disorder in a mammal that comprises administering to said mammal a therapeutically effective amount of a compound of Formula IV, or a stereoisomer or a pharmaceutically acceptable salt thereof, in combination with an anti-tumor agent selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, anti-androgens, targeted antibodies, HMG-CoA reductase inhibitors, and prenyl-protein transferase inhibitors.

Another embodiment provides compounds of Formula IV for use in therapy. In a further embodiment, the use also includes the use of a DNA damaging agent.

Another embodiment provides compounds of Formula IV for use in the treatment of a hyperproliferative disease. In a further embodiment, the hyperproliferative disease is cancer, including the above identified conditions. In a further embodiment, the use also includes the use of a DNA damaging agent.

The compounds of Formula IV can ben used in a pharmaceutical composition for inhibiting abnormal cell growth in a mammal, which composition comprises an amount of a compound of Formula IV, or a stereoisomer or a pharmaceutically acceptable salt thereof, in combination with an amount of a chemotherapeutic, wherein the amounts of the compound, stereoisomer or salt and of the chemotherapeutic are together effective in inhibiting abnormal cell growth. Many chemotherapeutics are known in the art. In certain embodiments, the chemotherapeutic is selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, anti-androgens, targeted antibodies, HMG-CoA reductase inhibitors, and/or prenyl-protein transferase inhibitors.

The compounds of Formula IV can ben used in a method for inhibiting abnormal cell growth in a mammal or treating a hyperproliferative disorder, in which the method comprises administering to the mammal an amount of a compound of Formula IV, or a stereoisomer or a pharmaceutically acceptable salt thereof, in combination with radiation therapy, wherein the amounts of the compound or salt, in combination with the radiation therapy is effective in inhibiting abnormal cell growth or treating the hyperproliferative disorder in the mammal. Techniques for administering radiation therapy are known in the art, and these techniques can be used in the combination therapy described herein. The administration of the compounds of Formula IV in this combination therapy can be determined as described herein.

It is believed that the compounds of Formula IV can render abnormal cells more sensitive to treatment with radiation for purposes of killing and/or inhibiting the growth of such cells. Accordingly, the compounds of Formula IV can ben used in to a method for sensitizing abnormal cells in a mammal to treatment with radiation, which method comprises administering to the mammal an amount of a compound of Formula IV or a stereoisomer or a pharmaceutically acceptable salt thereof, which amount is effective in sensitizing abnormal cells to radiation treatment. The amount of the compound, stereoisomer or salt to be used in this method can be determined according to means for ascertaining effective amounts of such compounds as described herein or by methods know to those skilled in the art.

Another embodiment provides the use of a compound of Formula IV, or a stereoisomer or pharmaceutically acceptable salt thereof, in the manufacture of a medicament for the treatment of hyperproliferative diseases. In a further embodiment, the hyperproliferative disease may be cancer, including the above identified conditions. In a further embodiment, the use also includes the use of a DNA damaging agent.

Another embodiment provides the use of a compound of Formula IV, in the manufacture of a medicament, for use as a CHK1 and/or CHK2 inhibitor in the treatment of a patient undergoing cancer therapy, including the above identified conditions, is provided. In a further embodiment, the use also includes the use of a DNA damaging agent.

Another embodiment o provides the use of a compound of Formula IV in the treatment of a hyperproliferative disease. In a further embodiment, the hyperproliferative disease is cancer, including the above identified conditions. In a further embodiment, the use also includes the use of a DNA damaging agent.

Another embodiment provides the use of a compound of Formula IV in the manufacture of a medicament, for use as a CHK1 and/or CHK2 inhibitor in the treatment of a patient undergoing cancer therapy. In a further embodiment, the use also includes the use of a DNA damaging agent.

In another embodiment, a pharmaceutical composition comprising a compound of Formula IV for use in the treatment of a hyperproliferative disease is provided.

In another embodiment, a pharmaceutical composition comprising a compound of Formula IV for use in the treatment of cancer is provided.

Combination Therapy

The compounds of Formula IV described herein can be used in and stereoisomers and pharmaceutically acceptable salts thereof may be employed alone or in combination with other therapeutic agents for treatment. The compounds of Formula IV can be used in combination with one or more additional drugs, for example an anti-inflammatory compound that works by a different mechanism of action. The second compound of the pharmaceutical combination formulation or dosing regimen preferably has complementary activities to the compound of Formula IV such that they do not adversely affect each other. Such molecules are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

EXAMPLE

In order to illustrate the invention, the following example is included. However, it is to be understood that this example does not limit the invention and is only meant to suggest a method of practicing the invention. Persons skilled in the art will recognize that the chemical reactions described may be readily adapted to alternative methods for preparing the compound of this invention which are deemed to be within the scope of this invention.

In the example described below, unless otherwise indicated all temperatures are set forth in degrees Celsius (° C.). Reagents were purchased from commercial suppliers such as Sigma-Aldrich Chemical Company, and were used without further purification unless otherwise indicated.

Preparation of
5-bromo-4-chloro-3-nitro-1H-pyrrolo[2,3-b]pyridine

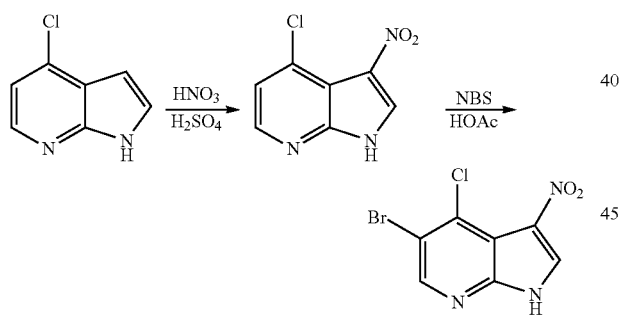

Step 1: Into concentrated sulfuric acid (150 mL) was added 4-chloro-1H-pyrrolo[2,3-b]pyridine (50.0 g) in portions while maintaining the internal temperature of the mixture below 10° C. (Note: exothermic upon addition). A mixture of concentrated nitric acid (30.0 mL) and concentrated sulfuric acid (60.0 mL) was added slowly while maintaining the internal temperature of the mixture below 10° C. (Note: exothermic upon addition). The reaction mixture was stirred at 0° C. for 30 min. Cold water (750 mL) was added slowly while maintaining the internal temperature below 20° C. (Note: exothermic upon addition). The resulting solid was collected by filtration and washed with a pH 7 buffer solution, water, and then acetonitrile. The product was collected by filtration and dried in a vacuum oven at 50° C. overnight to give the 52 g (92% yield) of 4-chloro-3-nitro-1H-pyrrolo[2,3-b]pyridine as an light yellow solid. $^1$H NMR (300 MHz, DMSO-d$_6$) δ 13.5 (s, 1H), 8.91 (s, 1H), 8.36 (d, J=5.2 Hz, 1H), 7.50 (d, J=5.2 Hz, 1H). $^{13}$C NMR (75 MHz, DMSO-d$_6$) δ 148.0, 145.7, 134.7, 132.5, 127.2, 120.9, 110.0. HRMS calcd. For C$_7$H$_3$ClN$_3$O$_2$ [M-H]$^-$: 199.9919, found 199.9921.

Step 2: Into a suspension of 4-chloro-3-nitro-1H-pyrrolo[2,3-b]pyridine (50.0 g) in acetic acid (300 mL) were added N-bromosuccinimide (NBS, 70.9 g, 1.60 equiv) in small portions at 25° C. The reaction mixture was stirred at 25° C. for 18 h. Water (3.0 mL) was added slowly over 30 min to get a light yellow slurry. The resulting solid was collected by filtration and washed with a 2:2:1 (v/v/v) mixture of saturated sodium sulfite solution, water, and methanol, followed by water and a 1:1 (v/v) mixture of methanol and water. The cake was dried in a vacuum at 50° C. oven overnight to give the 44.9 g (65% yield) of 5-bromo-4-chloro-3-nitro-1H-pyrrolo[2,3-b]pyridine as an light yellow solid. $^1$H NMR (300 MHz, DMSO-d$_6$) δ 13.7 (s, 1H), 8.93 (s, 1H), 8.66 (s, 1H). $^{13}$C NMR (75 MHz, DMSO-d$_6$) δ 146.9, 146.4, 133.9, 133.2, 127.0, 116.7, 111.3. HRMS calcd. For C$_7$H$_2$BrClN$_3$O$_2$ [M-H]$^-$: 273.9024, found 273.9031.

What is claimed:

1. A process for preparing 5-bromo-4-chloro-3-nitro-1H-pyrrolo[2,3-b]pyridine of Formula I:

comprising the step of subjecting 4-chloro-3-nitro-1H-pyrrolo[2,3-b]pyridine of Formula II to a bromination:

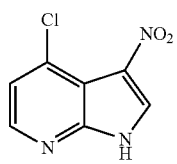

to yield 5-bromo-4-chloro-3-nitro-1H-pyrrolo[2,3-b]pyridine of Formula I.

2. The process of claim 1, wherein the bromination is performed using a solvent chosen among organic acids.

3. The process of claim 2, wherein the organic acid is acetic acid.

4. The process of claim 1, wherein bromination is performed by a brominating agent chosen from bromine, pyridinium tribromide, pyridinium dichlorobromate, 1,3-dibromo-5,5-dimethylhydantoin, tetrabromocyclohexadienone or N-Bromosuccinimide (NBS).

5. The process of claim 4, wherein the brominating agent is N-Bromosuccinimide (NBS).

6. The process of claim 1, comprising the steps of:
   (a) subjecting 4-chloro-1H-pyrrolo[2,3-b]pyridine of formula III:

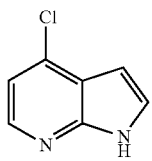

III to a nitration to yied 4-chloro-3-nitro-1H-pyrrolo[2,3-b]pyridine of Formula II:

II (b) subjecting 4-chloro-3-nitro-1H-pyrrolo[2,3-b]pyridine of Formula II to a bromination to yield 5-bromo-4-chloro-3-nitro-1H-pyrrolo[2,3-b]pyridine of Formula I.

7. The process of claim 6, wherein nitration is perfomed by using a nitrating agent chosen from nitric acid.

8. The process of claim 7, wherein nitration is performed under acidic conditions.

9. The process of claim 8, wherein nitration is preformed in the presence of sulfuric acid.

10. The process of claim 4, comprising the steps of:

(a) subjecting 4-chloro-1H-pyrrolo[2,3-b]pyridine of formula III:

III to a nitration to yied 4-chloro-3-nitro-1H-pyrrolo[2,3-b]pyridine of Formula II:

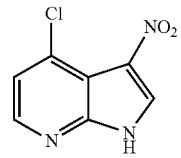

II (b) subjecting 4-chloro-3-nitro-1H-pyrrolo[2,3-b]pyridine of Formula II to a bromination to yield 5-bromo-4-chloro-3-nitro-1H-pyrrolo[2,3-b]pyridine of Formula I.

11. The process of claim 10, wherein nitration is perfomed by using a nitrating agent chosen from nitric acid.

12. The process of claim 11, wherein nitration is performed under acidic conditions.

13. The process of claim 12, wherein nitration is preformed in the presence of sulfuric acid.

14. The process of claim 13, wherein the organic acid is acetic acid.

15. The process of claim 14, wherein the brominating agent is N-Bromosuccinimide (NBS).

\* \* \* \* \*